(12) United States Patent
Stoddard et al.

(10) Patent No.: US 6,214,017 B1
(45) Date of Patent: Apr. 10, 2001

(54) ULTRASONIC SURGICAL APPARATUS

(75) Inventors: Robert Stoddard, Steamboat Springs; Arlan James Reschke, Longmont, both of CO (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 09/298,421

(22) Filed: Apr. 23, 1999

Related U.S. Application Data

(60) Provisional application No. 60/101,702, filed on Sep. 25, 1998.

(51) Int. Cl.[7] .................................................. A61B 17/22
(52) U.S. Cl. ............................................................ 606/128
(58) Field of Search ................................... 606/128, 169; 604/22

(56) References Cited

U.S. PATENT DOCUMENTS

| | | | |
|---|---|---|---|
| 3,990,452 | * 11/1976 | Murry et al. ............................ | 604/22 |
| 4,063,557 | 12/1977 | Wuchinich et al. . | |
| 4,223,676 | 9/1980 | Wuchinich et al. . | |
| 4,425,115 | 1/1984 | Wuchinich . | |
| 4,515,583 | 5/1985 | Sorich . | |
| 4,750,488 | 6/1988 | Wuchinich et al. . | |
| 4,750,901 | 6/1988 | Molteno . | |
| 4,827,911 | 5/1989 | Broadwin et al. . | |
| 4,922,902 | 5/1990 | Wuchinich et al. . | |
| 4,931,047 | 6/1990 | Broadwin et al. . | |
| 4,986,808 | * 1/1991 | Broadwin et al. ..................... | 604/22 |
| 5,015,227 | 5/1991 | Broadwin et al. . | |
| 5,038,756 | * 8/1991 | Kepley et al. ......................... | 604/22 |
| 5,242,385 | * 9/1993 | Strukel .................................. | 604/22 |
| 5,772,627 | * 6/1998 | Acosta et al. ......................... | 604/22 |
| 5,984,889 | * 11/1999 | Christ et al. .......................... | 604/22 |

FOREIGN PATENT DOCUMENTS

| | | |
|---|---|---|
| 0 384 672 | 8/1990 | (EP) . |
| 0 709 077 | 5/1996 | (EP) . |

* cited by examiner

*Primary Examiner*—Gene Mancene
*Assistant Examiner*—Eduando C. Robert

(57) ABSTRACT

An improved ultrasonic surgical apparatus includes an ultrasonic handpiece. An ultrasonic fragmenting tool is mountable within the handpiece, the tool having a vibratable tip adapted for ultrasonically fragmenting tissue at a surgical site of a patient. A transducer is mounted within the handpiece and coupled to a connector body. The connector body is coupled to the tip for transmitting ultrasonic waves to the tip from the transducer, the tip and the connector body being constructed of titanium or its alloys. An aspirating system is connected to the handpiece for aspirating fluid and tissue fragmented by the tip from the surgical site. An irrigation system is connected to said handpiece for supplying irrigation fluid to the surgical site for suspending fragmented tissue by the tip. Preferred embodiments include operational frequencies of about 36 kHz.

26 Claims, 10 Drawing Sheets

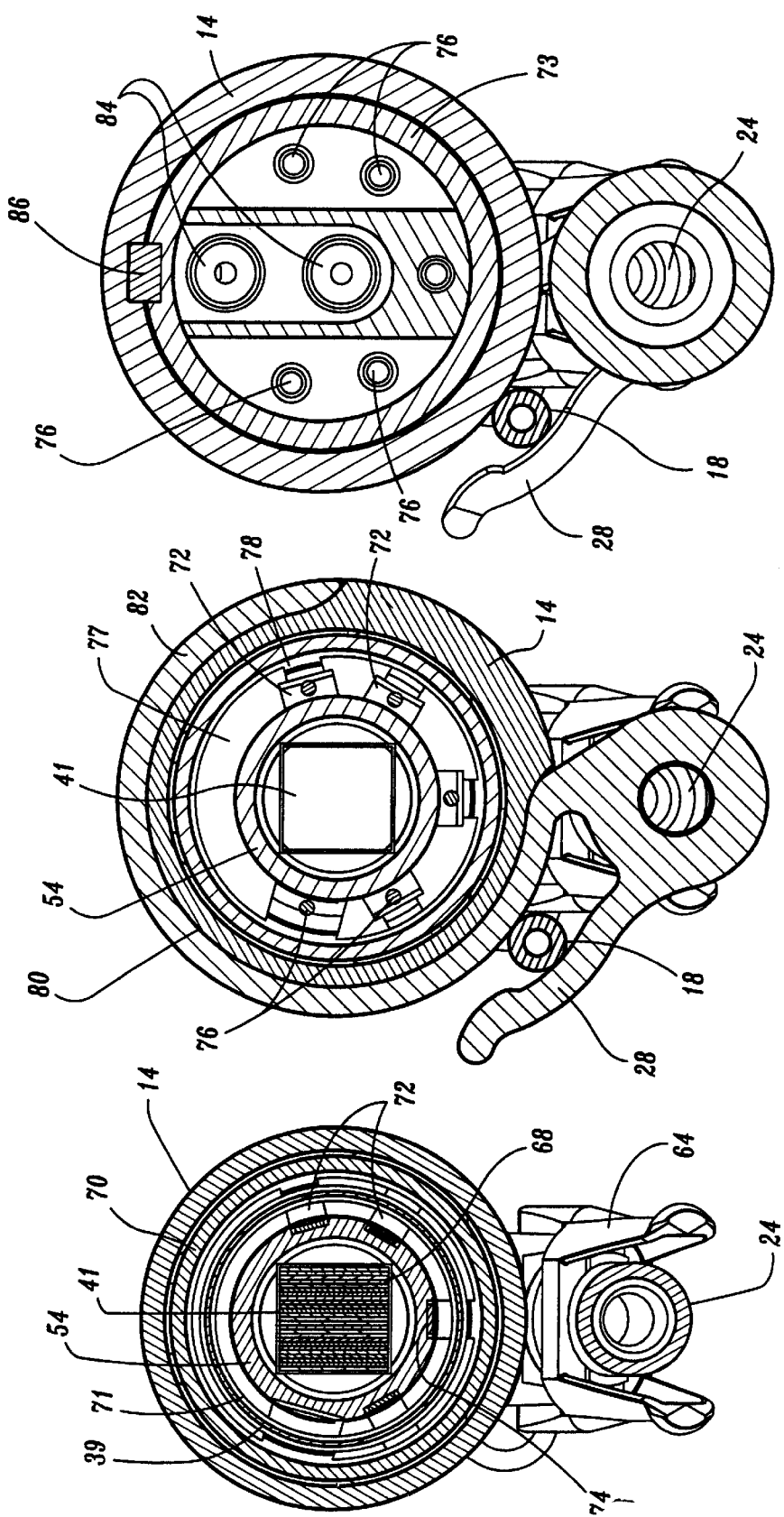

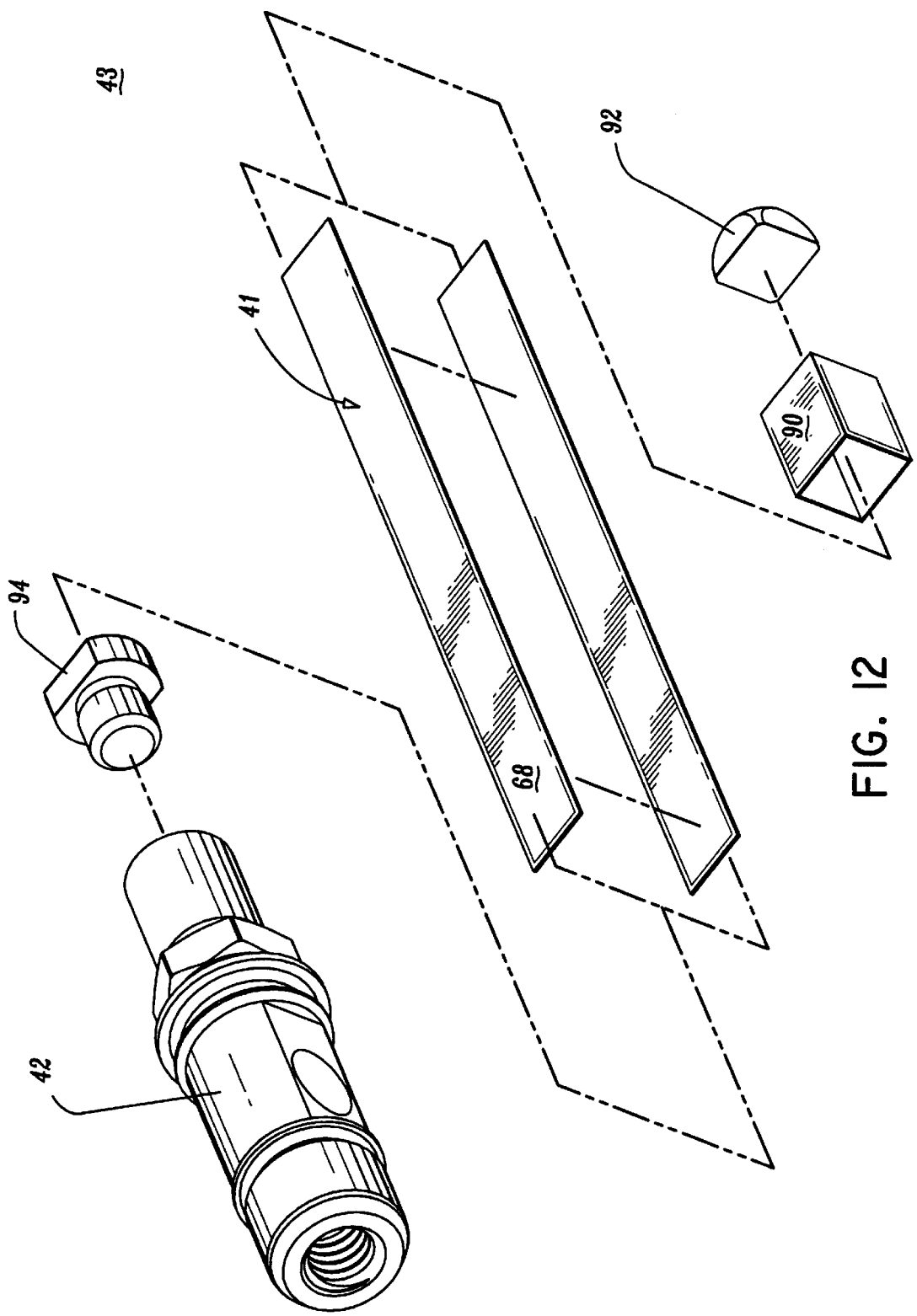

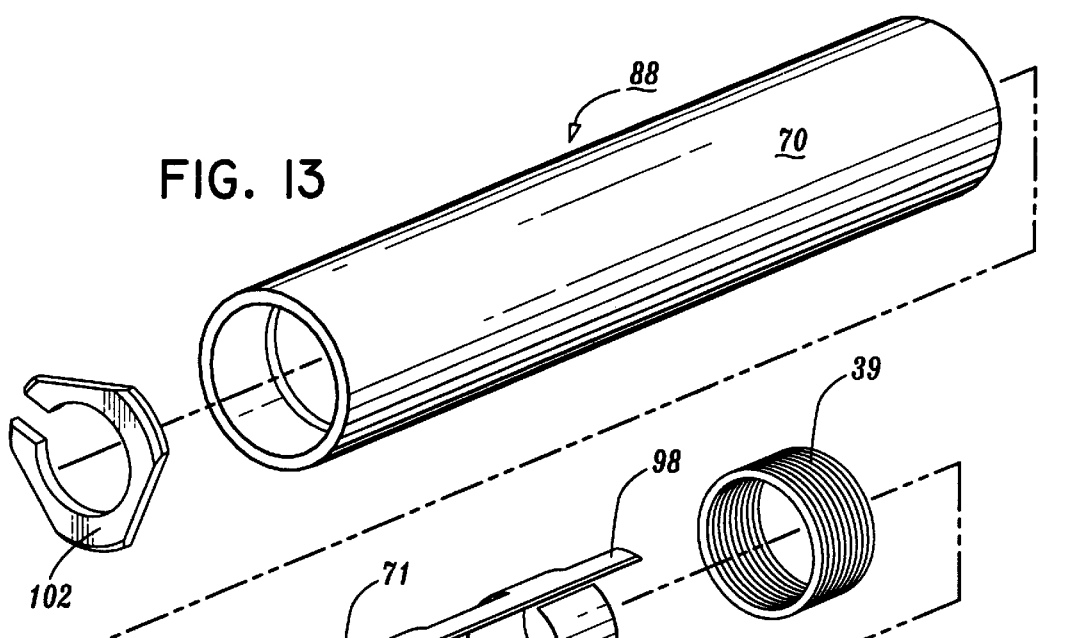
FIG. 13
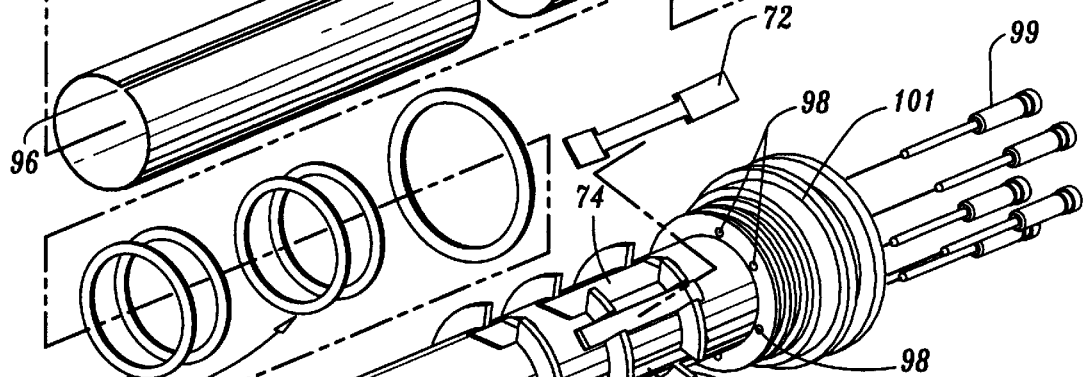
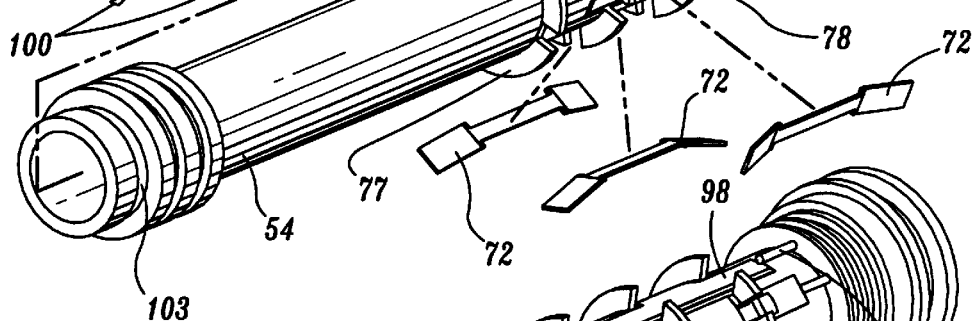
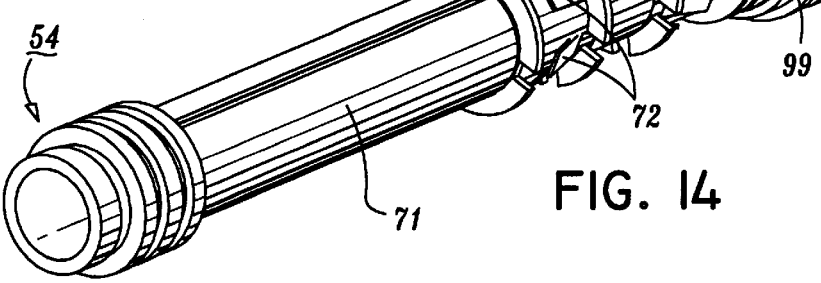
FIG. 14

ULTRASONIC SURGICAL APPARATUS

This application claims benefit to U.S. provisional application Ser. No. 60/101,702 filed Sep. 25, 1998.

BACKGROUND

1. Technical Field

This disclosure relates to surgical systems and, more particularly to an improved ultrasonic surgical apparatus for ultrasonically fragmenting tissue.

2. Background of Related Art

Devices which effectively utilize ultrasonic energy for a variety of applications are well-known in a number of diverse arts. The application of ultrasonically vibrating surgical devices used to fragment and remove unwanted tissue with significant precision and safety has led to the development of a number of valuable surgical procedures. Accordingly, the use of ultrasonic aspirators for the fragmentation and surgical removal of tissue from a body has become known. Initially, the technique of surgical aspiration was applied for the fragmentation and removal of cataract tissue. Later, such techniques were applied with significant success to neurosurgery and other surgical specialties where the application of ultrasonic technology through a handheld device for selectively removing tissue on a layer-by-layer basis with precise control has proven feasible.

Certain devices known in the art characteristically produce continuous vibrations having a substantially constant amplitude at a predetermined frequency (i.e 20–30 kHz). Certain limitations have emerged in attempts to use such devices in a broad spectrum of surgical procedures. For example, the action of a continuously vibrating tip may not have a desired effect in breaking up certain types of body tissue, bone, etc. Because the ultrasonic frequency is limited by the physical characteristics of the handheld device, only the motion available at the tip provides the needed motion to break up a particular tissue. The limited focus of such a device may render it ineffective for certain applications due to the vibrations which may be provided by the handheld device. For certain medical procedures, it may be necessary to use multiple hand held devices or it may be necessary to use the same console for powering different handheld devices.

Certain devices known in the art characteristically produce continuous vibrations having a substantially constant amplitude at a frequency of about twenty to about thirty kHz up to about forty to about fifty kHz. The amplitude is inversely proportional to frequency and directly proportional to wavelength. U.S. Pat. Nos. 4,063,557, 4,223,676 and 4,425,115 disclose devices suitable for the removal of soft tissue which are particularly adapted for removing highly compliant elastic tissue mixed with blood. Such devices are adapted to be continuously operated when the surgeon wishes to fragment and remove tissue, and generally is operated by a foot switch.

A known instrument for the ultrasonic fragmentation of tissue at an operation site and aspiration of the tissue particles and fluid away from the site is the CUSA model System 200 Ultrasonic Aspirator manufactured and sold by Valleylab, Inc. of Boulder, Colo., a subsidiary of U.S. Surgical Corporation; see also U.S. Pat. No. 4,827,911. When the longitudinally vibrating tip in such an aspirator is brought into contact with tissue it gently, selectively and precisely fragments and removes the tissue. Advantages of this unique surgical instrument include minimal damage to healthy tissue in a tumor removal procedure, skeletoning of blood vessels, prompt healing of tissue, minimal heating or tearing of margins of surrounding tissue, with minimal pulling of healthy tissue, and excellent tactile feedback for selectively controlled tissue fragmentation and removal is provided.

In many surgical procedures where ultrasonic fragmentation instruments are employed additional instruments are required for tissue cutting and hemostasis at the operation site. For example, hemostasis is needed in desiccation techniques for deep coagulation to dry out large volumes of tissue and also in fulguration techniques for spray coagulation to dry out the surface of tissues.

The apparatus disclosed in U.S. Pat. Nos. 4,931,047 and 5,015,227 provide hemostasis in combination with an ultrasonically vibrating surgical fragmentation instrument and aspirator. The apparatus effectively provide both a coagulation capability and an enhanced ability to fragment and aspirate tissue in a manner which reduces trauma to surrounding tissue.

U.S. Pat. No. 4,750,488 and its two continuation Patents, 4,750,901 and 4,922,902 disclose methods and apparatus which utilize a combination of ultrasonic fragmentation, aspiration and cauterization.

In an apparatus which fragments tissue by the ultrasonic vibration of a tool tip, it is desirable, for optimum efficiency and energy utilization, that the transducer which provides the ultrasonic vibration should operate at resonant frequency. The transducer design establishes the resonant frequency of the system, while the generator tracks the resonant frequency. The generator produces the electrical driving signal to vibrate the transducer at resonant frequency. However, changes in operational parameters, such as, changes in temperature, thermal expansion and load impedance, result in deviations in the resonant frequency. Accordingly, controlled changes in the frequency of the driving signal are required to track the resonant frequency. This is controlled automatically in the generator.

During surgery, fragmentation devices, such as the handpieces described above, are used internally to a patient. A surgeon manipulates the handpiece manually at an operative site, and therefore the handpiece itself may reduce visibility of the operative site. It would therefore be advantageous to provide an apparatus with the above described features with a smaller profile such that a greater field of view is provided for the surgeon at the operative site.

SUMMARY

An improved ultrasonic surgical apparatus having reduced size includes an ultrasonic handpiece. An ultrasonic fragmenting tool is mounted within the handpiece, the tool having a vibratable tip adapted for ultrasonically fragmenting tissue at a surgical site of a patient. A transducer is mounted within the handpiece and coupled to a connecting body. The connecting body is coupled to the tip for transmitting ultrasonic waves to the tip from the transducer, the tip and the connecting body being constructed of titanium or its alloys. An aspirating system is connected to the handpiece for aspirating fluid and tissue fragmented by the tip from the surgical site. An irrigation system is connected to said handpiece for supplying irrigation fluid to the surgical site for suspending fragmented tissue by the tip.

Another improved ultrasonic surgical apparatus having reduced size includes an ultrasonic handpiece. An ultrasonic fragmenting tool is mounted within the handpiece, the tool having a vibratable tip adapted for ultrasonically fragmenting tissue at a surgical site of a patient. A transducer is mounted within the handpiece and coupled to a connecting body. The connecting body is coupled to the tip for transmitting ultrasonic waves to the tip from the transducer, the connecting body is coupled with the tip for transmitting ultrasonic waves at a frequency of at least 35,000 Hz to the tip from the transducer. An aspirating system is connected to the handpiece for aspirating fluid and tissue fragmented by the tip from the surgical site. An irrigation system is connected to said handpiece for supplying irrigation fluid to the surgical site for suspending fragmented tissue by the tip.

In alternate embodiments of the ultrasonic surgical apparatus systems described, the transducer may include a stack of magnetostrictive plates longitudinally disposed within the handpiece and responsive to an input frequency for vibrating the tip. The plates can be flat or gusseted and may be fabricated of nickel or alloys thereof. The entire acoustic vibrating assembly (the transducer and its associated components) determines the system frequency. A fluid supply for introducing cooling fluid to the fragmenting tool and/or the transducer may also be provided. The aspiration system may include a detachable aspiration line wherein the aspiration line is removable from the handpiece. The tip may include a cavity formed therein in fluid communication with at least one inlet port positionable at a location adjacent to the surgical site wherein the aspiration system aspirates fluid and tissue fragmented by the tip from the surgical site through the inlet port and the cavity. The handpiece is preferably between about 4.5 and about 6 inches in length, and is preferably cylindrical and between about 0.5 and about 0.7 inches in diameter. The transducer produces standing waves having a wavelength, $\lambda$, and the transducer may have a length of about $\lambda/2$, the tip have a length of about $\lambda/4$ and the connecting body may have a length of about $\lambda/4$.

These and other objects, features and advantages of the present disclosure will become apparent from the following detailed description of illustrative embodiments thereof, which is to be read in connection with the accompanying drawings.

BRIEF DESCRIPTION OF THE DRAWINGS

Various embodiments are described herein with reference to the drawings, wherein:

FIG. 9 is a cross-sectional view taken at section line 9—9 of FIG. 3 showing a stack of plates for an ultrasonic transducer;

FIG. 10 is a cross-sectional view taken at section line 10—10 of FIG. 3 showing conductors for activating the transducer;

FIG. 11 is a cross-sectional view taken at section line 11—11 of FIG. 3 showing ports and receptacles for supplying cooling fluid and power, respectively to the apparatus;

FIG. 12 is a perspective view with parts separated of a stack assembly;

FIG. 13 is a perspective view with parts separated of a transducer coilform assembly;

FIG. 14 is a perspective view of a partially assembled transducer coilform assembly;

DETAILED DESCRIPTION OF PREFERRED EMBODIMENTS

The present disclosure is directed to an apparatus for ultrasonically fragmenting and aspirating tissue in a surgical operation. The apparatus includes a handpiece used by a surgeon to direct fragmentation. The handpiece includes an ultrasonically actuated tip which fragments tissue to be carried away by an aspiration system. An irrigation system which provides cooling fluid to the tip is provided for maintaining temperature within an acceptable range. A cooling system for supplying cooling fluid to the internal active components of the handpiece may also be provided. The handpiece is advantageously reduced in size to permit better maneuverability by a surgeon and to permit a larger field of view during internal surgery through an open incision.

Figure 1:
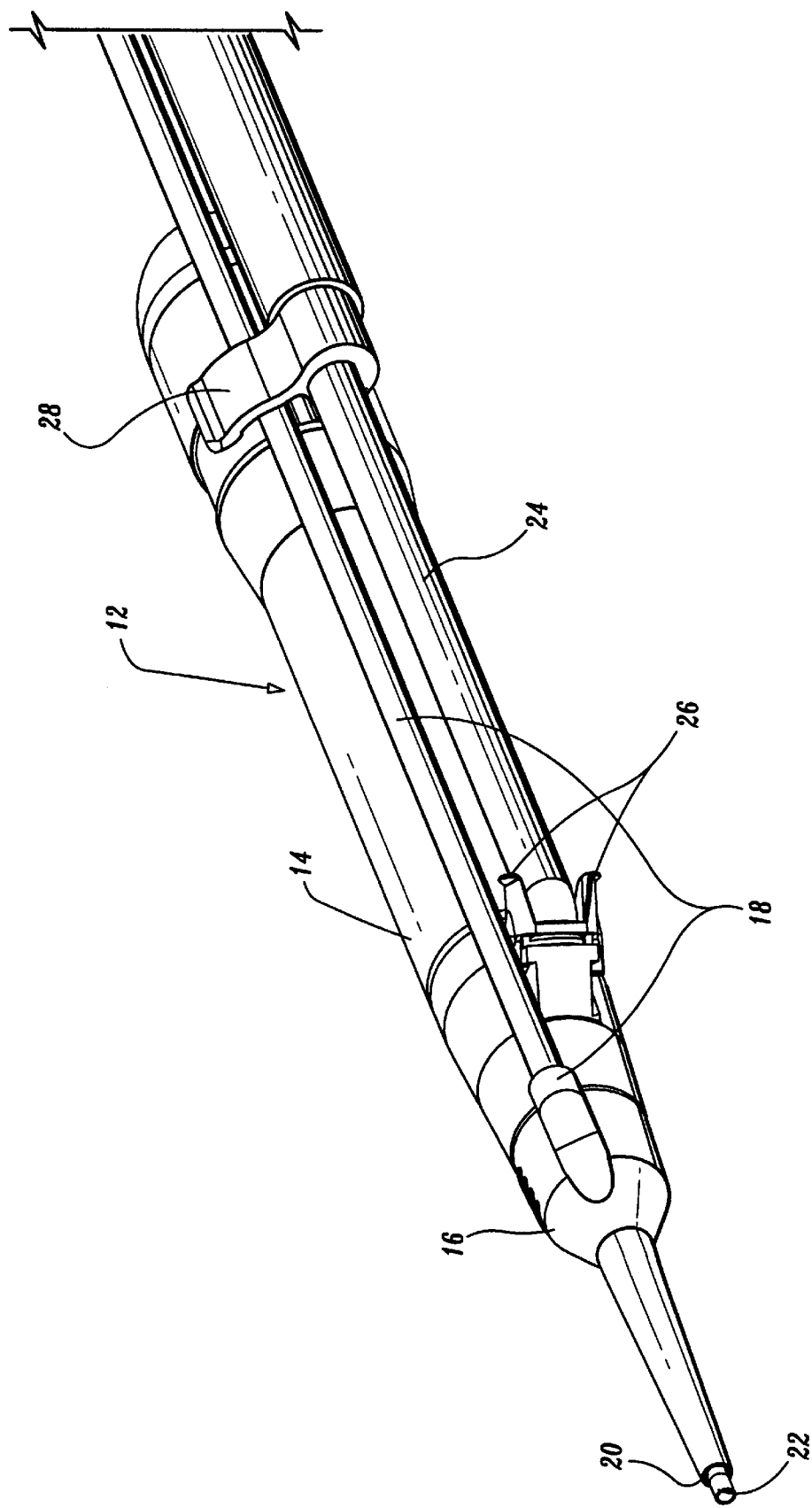
FIG. 1 is a perspective view of an ultrasonic surgical apparatus constructed in accordance with the present disclosure.
Figure 2:
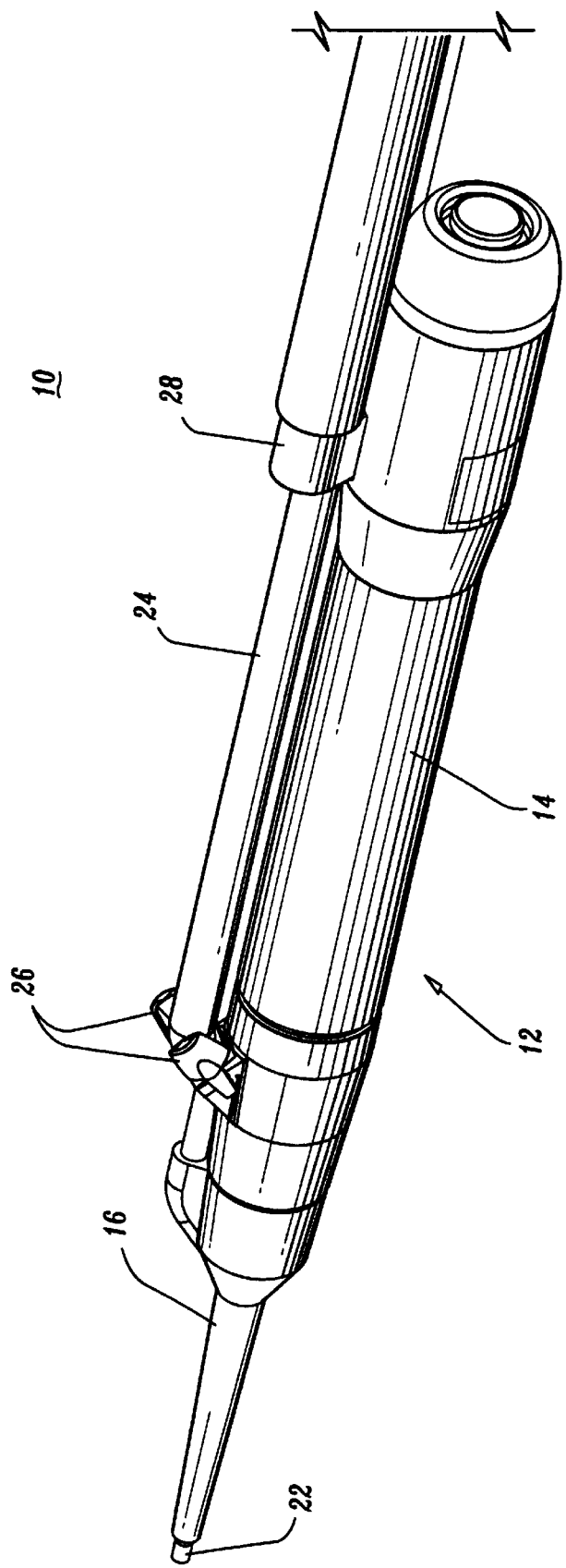
FIG. 2 is another perspective view of the ultrasonic surgical apparatus of FIG. 1 in accordance with the present disclosure.
Figure 3:
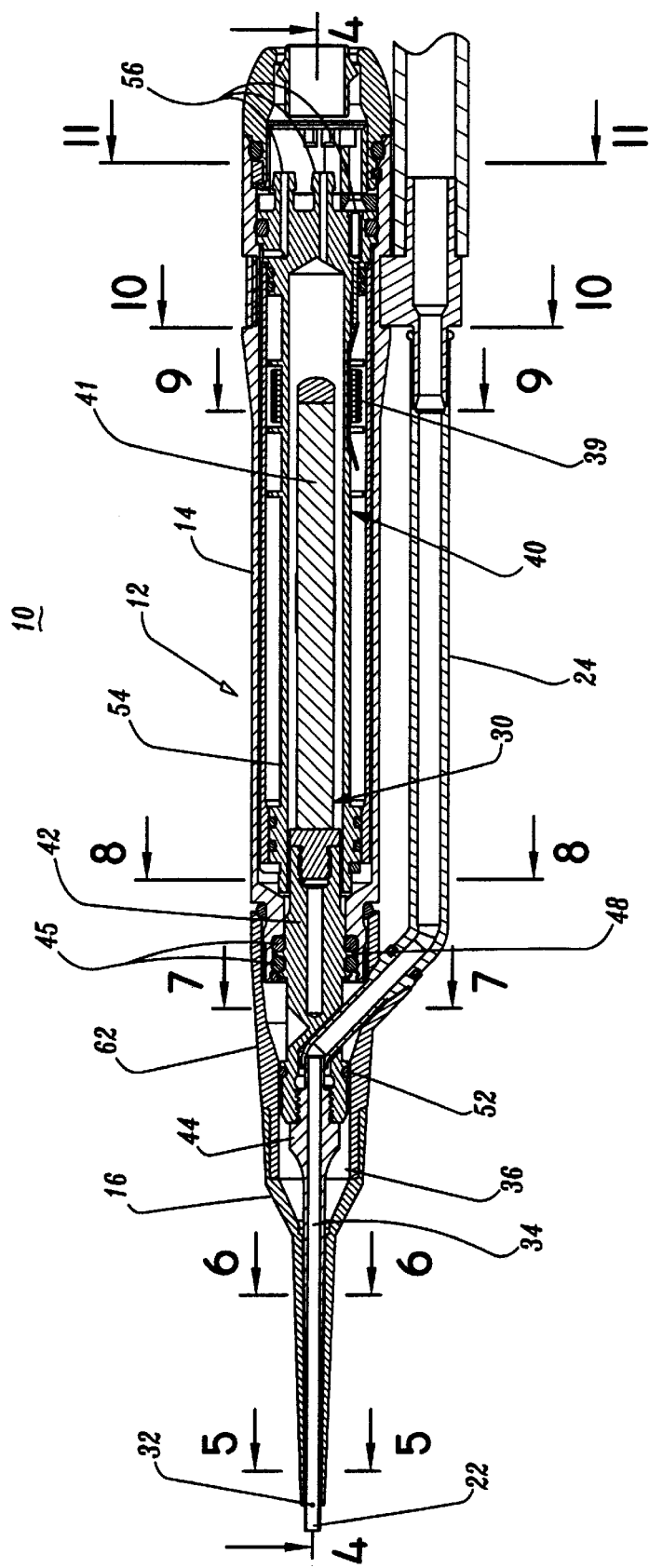
FIG. 3 is a side cross-sectional view of the surgical apparatus of FIG. 1.

Referring now in specific detail to the drawings in which like reference numerals identify similar or identical elements throughout the several views, and initially to FIGS. 1 and 2, one embodiment of an apparatus for ultrasonically fragmenting and aspirating tissue is shown generally as apparatus 10. Apparatus 10 is embodied in a conveniently held handpiece 12, a longitudinal cross-sectional view of which is shown in FIG. 3 of the drawings. Handpiece 12 includes a housing 14 which may be a sterilizable plastic or metal, preferably plastic. Housing 14 connects to an irrigation flue 16 at a distal end portion. Flue 16 includes an irrigation port and connection line 18 therein communicating with an opening 20 at a distal end thereof. A tip 22 is shown at a distal end of handpiece 12. Tip 22 is vibrated to fragment tissue during surgery as will be described in further detail hereinbelow.

An aspiration line 24 is shown mounted externally to housing 14. Aspiration line 24 includes release tabs 26 for dismounting a distal end portion of aspiration line 24. Further, a tab 28 is included on a proximal end portion of aspiration line 24. Tabs 26 and 28 secure aspiration line 24 and irrigation line 18 to housing 14 and permit detachment of aspiration line 24 and irrigation line 18 from housing 14.

Handpiece 12 is advantageously significantly reduced in size over known handpieces and provides additional tissue selectivity and better visibility in accordance with the present disclosure. Handpiece 12 is dimensioned at about 4.5 to about 6 in length and about 0.5 to about 0.7 in diameter. This represents at least a 30% reduction in length and width thereby making handpiece more maneuverable and more easily handled by a surgeon during use.

Figure 4:
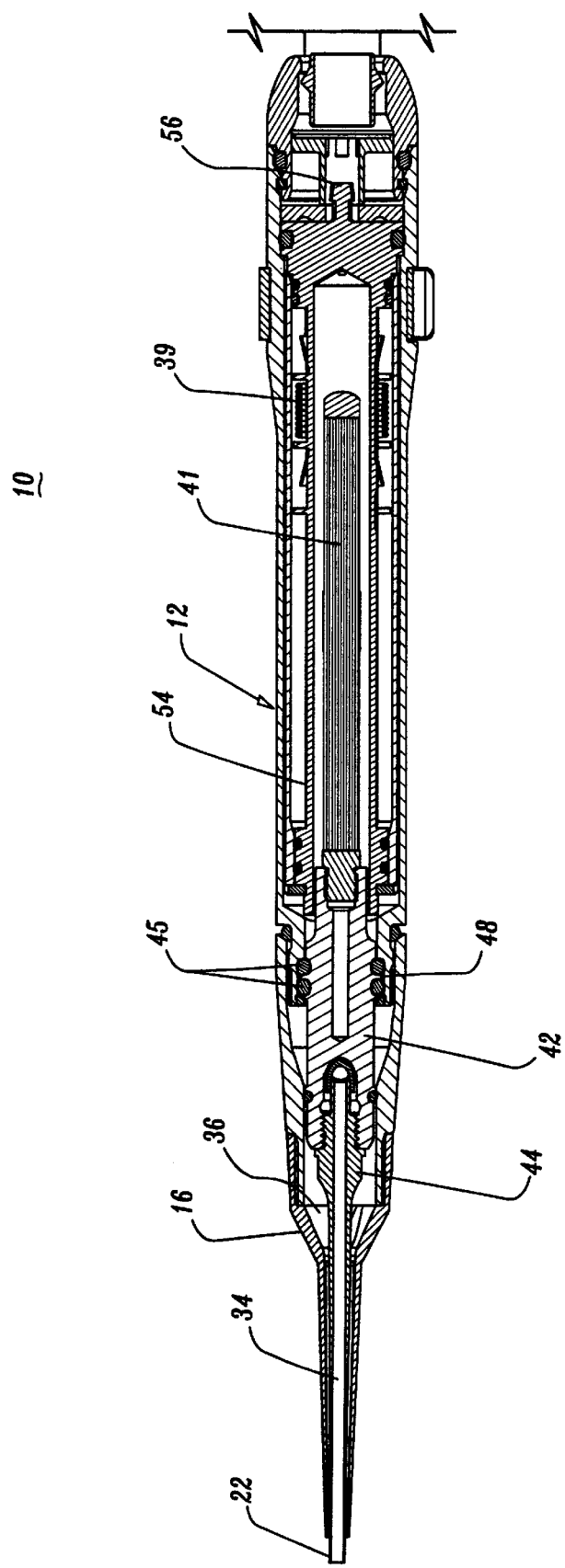
FIG. 4 is a top cross-sectional view of the surgical apparatus of FIG. 1.

Referring to FIGS. 3 and 4, side (FIG. 3) and top (FIG. 4) longitudinal cross-sectional views of handpiece 12 are shown. Housing 14 encloses a resonant vibrator 30 to vibrate in the ultrasonic range, including an aspirating tool vibrating at its tip in the ultrasonic frequency range at a longitudinal amplitude in excess of about 5 mils (0.005 inch). To achieve such an effect in an instrument which can be conveniently held by a surgeon, transmission of excitation to tip 22 is performed at the same time such tip 22 acts as an aspirating inlet to effect the surgical removal of the undesired tissue through cavity 34. A preaspiration hole or inlet 32 communicates with cavity 34 within tip 22. During operation, irrigation fluid is supplied through irrigation port 18 into flue 16. Flue 16 and tip 22 form an annular cavity 36 therebetween. Irrigation fluid is supplied to the distal end of tip 22, drawn into inlet 32, and removed by the aspiration system through cavity 34 and aspiration line 24. Tissue and blood from the surgical site are removed through the distal opening to the cavity 34.

Where highly compliant tissue mixed with blood is aspirated, there is the increased likelihood of occlusion of the aspiration conduit due to the coagulation of the blood. It is therefore desirable to provide as large an aspiration path as possible. In addition, vibration apparently acts to increase the rate of coagulation. It is therefore additionally desirable that the aspiration path or conduit should preferably have minimal changes of direction of flow and where such changes are required, they should be as gentle as possible.

Referring now to construction of the resonant vibrator 30, vibrator 30 functions as a mechanical vibrating system mounted in handpiece 12. The vibrating system includes a transducer 40 having a magnetostrictive stack 41 preferably composed of a nickel alloy sandwich of flat or gusseted nickel alloy plates responsive to magnetic fields. Electrical oscillating current supplied to a winding of a coil 39 induces mechanical oscillations in transducer 40, such oscillations preferably being at the resonant frequency and having a maximum practical peak-to-peak stroke (amplitude) of about 0.0002 thousandth of an inch (0.2 mils) at a frequency of about 36 kHz. Due to limitations imposed by the physics of the system, as frequency increases in the ultrasonic range, the stroke that one is able to obtain in the transducer is reduced.

However, it is known in the art that if one desires to take the available stroke from the transducer and vary the stroke, an ultrasonic mechanical transformer may be used. The design of such a transformer which is fixedly attached to the transducer magnetostrictive stroke is taught, for instance, in U.S. Pat. No. RE 25,033, incorporated herein by reference.

The design of the transformer section must include and yield the preferred characteristics at the output portion of resonant vibrator 30. In this regard, the output portion of vibrator 30 (the distal end of tool 44) may vibrate ultrasonically with a desired stroke (peak to peak) of at least 0.005 to 0.0085 inch (5–8.5 mils). The output portion may also, for surgical requirements, be rather long and slender, while for aspiration purposes it is preferred to have as large a cross-sectional flow area as possible to thereby minimize the possibility of occluding the aspiration conduit.

Resonant vibrator 30 further includes a connecting body 42 and a tool 44. Stack 41, connecting body 42 and tool 44 function as a three body system. It is therefore advantageous to have lengths of these bodies proportional to the half wavelength of the resonant frequency. The entire system length has a length equal to a multiple of $\lambda/2$. An increase in frequency permits a reduction in overall length. ($\lambda=c/$ frequency). In a preferred embodiment, lengths of stack 41, connector body 42 and tool 44 are about $\lambda/2, \lambda/4$ and $\lambda/4$, respectively. As handpiece 12 is held and manipulated by the surgeon in one of his hands, the size and weight of handpiece 12 is limited by the ability of the hand to delicately grasp and manipulate the instrument. Since handpiece 12 is desirably reduced in size to permit better control by the surgeon and to increase the surgeon's field of view during surgery, a reduced size apparatus 10 is preferred. A reduction in size of apparatus 10 is difficult to achieve due to physical limitations. Merely downsizing the components of prior art handpieces will result in a design deficient of power (minimal tip displacement) but with high gain (defined as displacement amplitude of a tool over the displacement amplitude of a connector body).

Proportionality to resonant wavelength as well as increased frequency due to reduced size are addressed by apparatus 10 by providing a shorter instrument having increased frequency. Advantageously, connecting body 42 and tool 44 are provided having a substantially similar density material which is high in strength. In so doing, power (tip displacement) is increased dramatically for tool 44 at the cost of gain. Surprisingly, gain is still markedly increased in apparatus 10 over the prior art handpieces despite this reduction. Tool 44 includes tip at its distal end portion. Therefore, tip 22 experiences the maximum amplitude of tool 44. Displacements achieved reached between about 0.005 and about 0.0085 inch. Displacements of this amplitude were achieved for frequencies of about 35 kHz or greater.

High strength materials are preferred to handle stress induced in tool 44 and connecting body 42 at the above frequency. Therefore, metals such as titanium and its alloys are preferred. Further, since tool 44 is subjected to high stresses, tool 44 is tapered over most of its length to preferably reduce the stress to which the metal is subjected. Coatings may be applied to tool 44 to improve their characteristics.

Tool 44, in terms of its length and its distributed mass, is a dynamic part of the resonant vibrator 30 which can magnify the 0.0002 inch stroke input induced in the magnetostrictive stack of transducer 40 to in excess of a 0.005 inch output at tip 22. Connecting body 42 is a unitary structure also dynamically a part of resonant vibrator 30 which serves to connect transducer 40 to tool 44 and, more importantly, to serve to transmit and modify the stroke as it is dynamically transmitted from transducer to tool.

A node of motion of resonant vibrator 30 is located in the vicinity of the distal end of connecting body 42 at the interface between the connecting body 42 and the tool 44. Nodes are locations of high stress and minimal displacement due to the standing waves ultrasonically produced by the transducer. Higher frequencies provide greater tissue selectivity during surgery. Also, power is increased (displacement) by applying increased strain to the materials of tool 44 and connecting body 42.

Power equals force times velocity, and force is proportional to the product of stress and area. Thus, to maximize power of the mechanical resonant structure, the force in the system should be maximized by designing the system components to their endurance strength. The velocity of the resonant structure should also be maximized by maximizing displacement. This can be accomplished by designing as low of a gain vibrator (connecting body 42 and stack 41) that still allows for the desired displacement at the distal end of the tool 44.

Handpiece 12 which includes vibrator 30 and connecting body 42 mounted therein may advantageously be reduced in size by using high strength materials having a substantially similar density for both tool 44 and connecting body 42. A size reduction of about 30% can be achieved in so doing as well as an increased frequency of operation. Such reduction is size permits a surgeon to conveniently hold handpiece 12 in one hand and manipulate it more accurately for improved results during surgery, for example neurosurgery.

Connecting body 42 has flange 48 which functions to position the vibrator 30 in handpiece 12. Flange 48 has O-rings 45 disposed thereabout thereby sealing and separating off a distal end portion of housing 14 for cooling fluid circulation. O-ring 52 engages connecting body 42 and seals irrigation fluid in flue 16. Tool 44 and stack 41 threadably engage connector body 42 as shown in FIG. 3.

During operation of handpiece 12, heat is generated. To remove this heat, a transducer housing (coilform) 54 houses stack 41 and includes ports 56 at a proximal end portion for accessing stack with a cooling fluid to lower temperatures therein. Housing 54 further includes access ports 56 for supplying power to circuitry of transducer 40.

Figure 5:
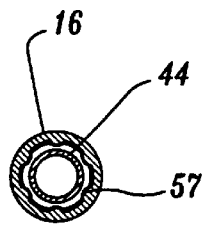
FIG. 5 is a cross-sectional view taken at section line 5—5 of FIG. 3 showing a tip and a manifold in operative relationship.
Figure 6:
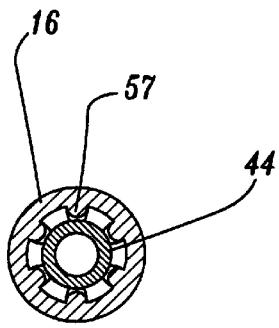
FIG. 6 is a cross-sectional view taken at section line 6—6 of FIG. 3 showing the tip and the manifold.

FIGS. 5 and 6 are transverse cross-sectional views of tool 44 taken through section lines 5—5 and 6—6 in FIG. 3, respectively. Tool 44 is substantially circular and disposed within flue 16 (FIG. 5). Flue 16 supplies irrigation fluid to an operative site during surgery (FIG. 6). Since flue 16 is a hollow member, ridges 57 are included for strength and may contact tool 44. Ridges 57 help to maintain flue 16 and tool 44 concentric.

Figure 7:
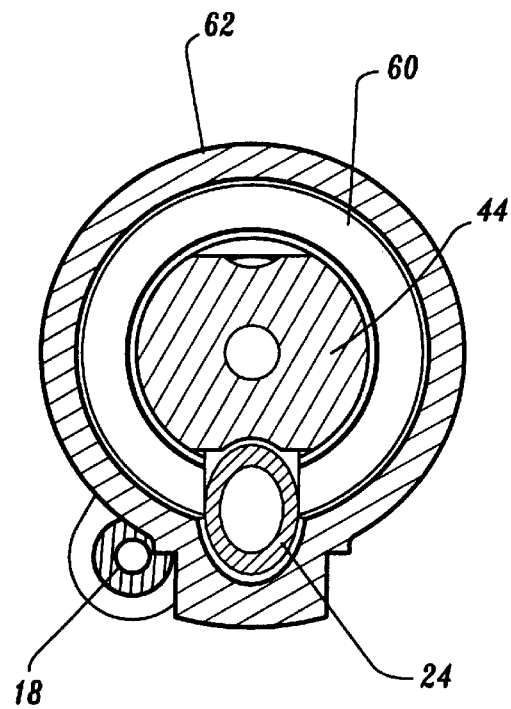
FIG. 7 is a cross-sectional view taken at section line 7—7 of FIG. 3 showing a connector body and an aspiration line.

FIG. 7 is a transverse cross-sectional view through connector body 42 taken at section lines 7—7 indicated in FIG. 3. Aspiration line 24 communicates with cavity 34 of tool 44 by passing through connector body 42. A space 60 is defined between connector body 42 and a cap 62 which engages flue 16 (FIG. 3) to permit vibrations of the system without contact between cap 62 and connector body 42. Also, irrigation port 18 is shown.

Figure 8:
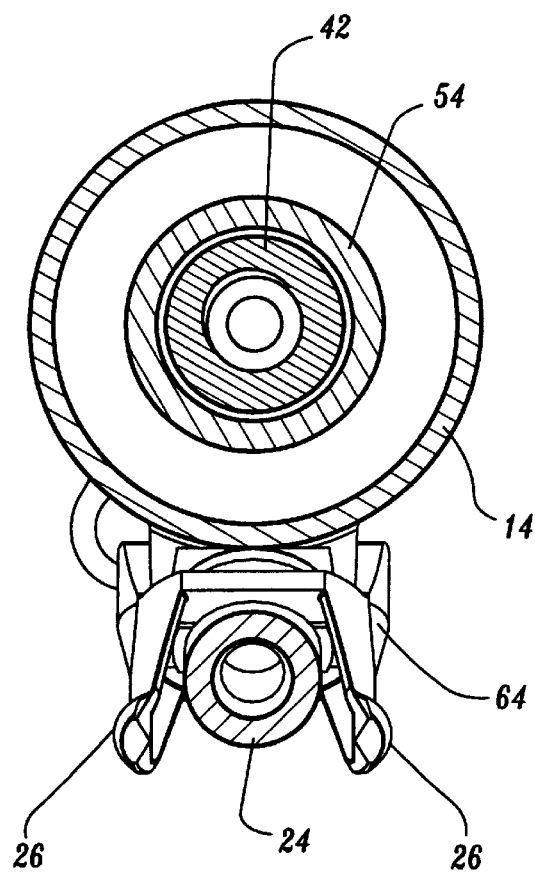
FIG. 8 is a cross-sectional view taken at section line 8—8 of FIG. 3 showing the connector body and the aspiration line.

Referring to FIG. 8, a transverse cross-sectional view of connector body 42 is shown section lines 8—8 indicated in FIG. 3. Connecting body 42 is shown spaced apart from transducer housing 54 to permit vibrations therebetween. Aspiration line 24 is shown having a coupling 64 for releasing aspiration line 24 when tabs 26 are depressed.

FIG. 9, a cross-sectional view taken along section line 9—9 in FIG. 3, illustrates stack 41 having a plurality of magnetostrictive plates 68. Stack 41 is disposed within transducer housing 54 which is disposed within a tube 70. Conductors 72 are disposed in grooves 74 formed in transducer housing 54. A conductive sheet 71 surrounds conductors 72. Coil 39 is wrapped about transducer housing 54 for extending a magnetic field created by coil 39. Housing 14 is also shown.

Referring to FIG. 10, a proximal end of stack 41 is shown as well as proximal ends of conductors 72. Engagement pins 76 are shown in cross-section and engage conductors 72 to make an electrical connection thereto. Transducer housing 54 has flanges 77 extending therefrom with openings 78 formed in each flange to receive conductors 72. A recess 80 formed in housing 14 receives a clip 82 for securing aspiration line 24 to housing 14. Tab 28 on clip 82 is used to secure the flue tube 18 on the handpiece housing 14. Clip 82 may be detached from housing 14 by unclipping.

As is shown in FIG. 11, engagement pins 76 are dimensioned and configured to receive plugs (not shown) of an electrical connector to supply power to stack 41 through conductors 72 and coil 39 (FIG. 3). Two ports 84 are provided for providing access to cavity adjacent to stack 41. Cooling fluid may be introduced and removed as a heat transfer medium to reduce temperatures of stack 41 during operation. An antirotation block 86 is included to prevent rotation of end cap 73 within housing 14. Aspiration line 24 includes a larger diameter tube thereon to provide easier maintenance of suction at the operative site.

A stack assembly 43 is shown in exploded detail in FIG. 12. Stack 41 is assembled by stacking and connecting plates 68 and applying a sleeve 90 and an end cap 92 thereto. A threaded end cap 94 connects to a distal end portion of stack 41. End cap 94 threadedly engages connector body 42. The elements of stack assembly 43 may be brazed together to prevent separation.

Referring to FIGS. 13 and 14, an exploded and assembled view of a transducer housing assembly 88 is shown. Transducer housing (coilform) 54 includes grooves 74 and flanges 77 with openings 78 for receiving conductors 72 therein. Conductive sheet 71 is placed around coilform 54. Engagement pins 76 are inserted into holes 98 formed in a proximal end portion of transducer housing (coilform) 54. Pins 76 engage conductors 72 which provide electrical current to and thereby activate coil 39. Sheet 71 is preferably a high conductivity metal, such as copper. Sheet 71 includes an extended portion 98 for connection to engagement pins 76. Current is supplied by engagement pins 76 to conductors 72 passed through coil 39 and returned through other conductors 72 and engagement pins 76. In this way current is directed through the coil 39 to create a magnetic flux.

Transducer housing (coilform) 54 is inserted within tube 70 and engages a flange 101 at a proximal end portion of housing 54. Housing 54 is maintained and sealed within tube 70 by 0-rings 100. A fastener 102 further secures transducer housing 54 in tube 70 at its distal end portion by snapping into a groove 103 on the distal end portion of housing 54. FIG. 14 shows transducer housing 54 partially assembled to show the placement of sheet 71 and conductors 72. Extended portion 98 engages return pin 99 while the remaining pins 76 engage conductors 72.

Figure 15:
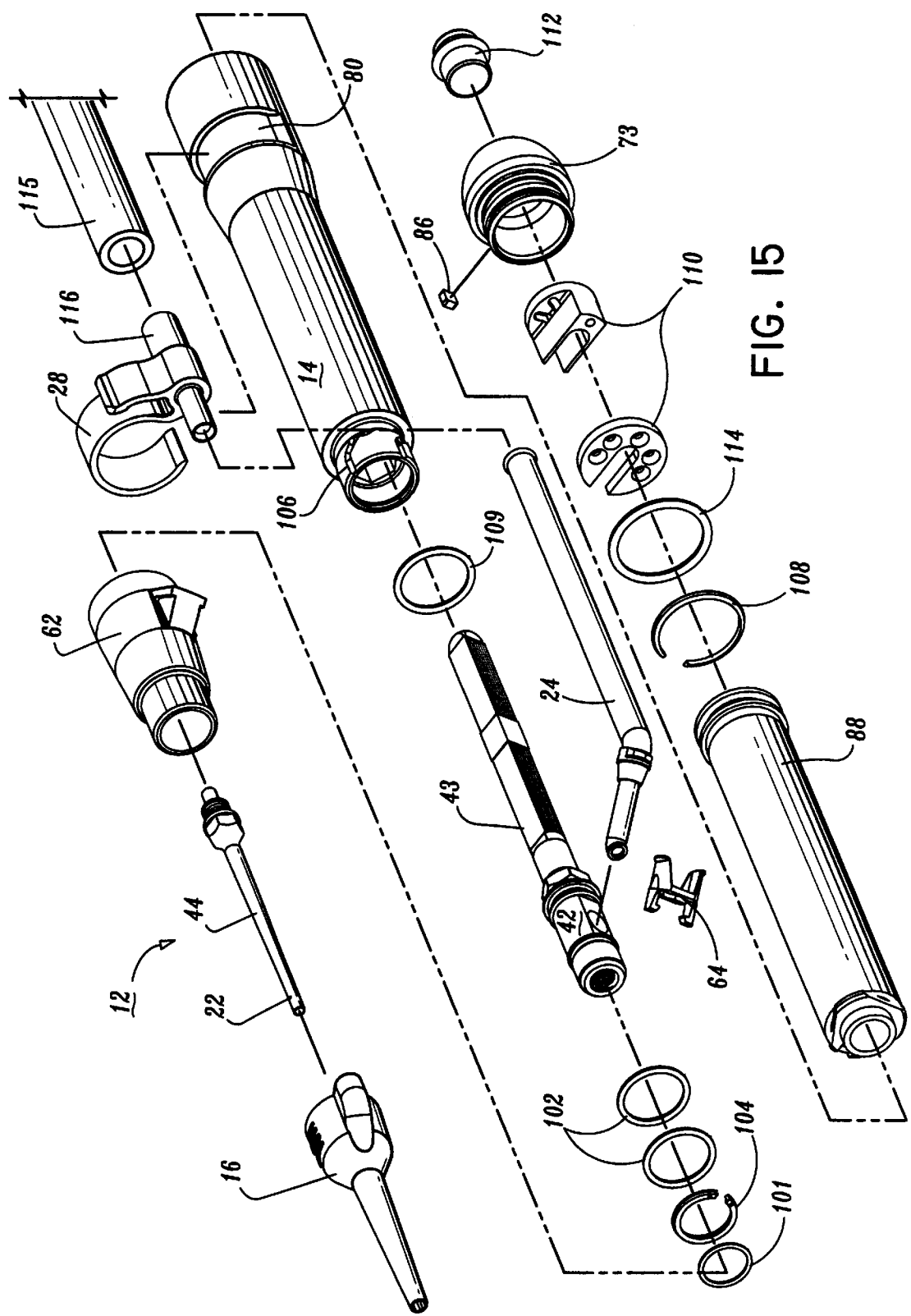
FIG. 15 is a perspective view with parts separated of a handpiece in accordance with the present disclosure.

FIG. 15 shows assembly of handpiece 12 by threading tool 44 into stack assembly 43 to form the three masses for vibrator 30 (FIG. 3). Transducer housing assembly 88 is inserted in housing 14 and stack assembly 43 and transducer housing assembly 88 are attached to housing 14. The interface between tool 44 and connecting body 42 is positioned near a node. Stack assembly 43 is slid into transducer housing assembly 88 inside housing 14. At the connection area between stack assembly 43 and housing assembly 88, O-ring seals 102 are used and secured by a clip 104 within an opening in the distal end portion of housing 14. Cap 62 is coupled to housing 14 by a bayonet type coupling 106. An O-ring 101 seals a distal end portion of the connector body 42 to cap 62. A proximal end portion of cap 62 is sealed off with O-ring 109. Flue 16 is attached to cap 62.

Guide plates 110 communicate with ports 56 (FIG. 3) and engagement pin 76 locations (FIG. 3) to permit engagement by a plug (not shown) to supply cooling fluid and power to transducer assembly 88. End cap 73 and a plug 112 fit into distal end portion of housing 14. An O-ring 114 provides a seal between end cap 73 and housing 14.

Aspiration line 24 is connecting to connecting body 42 in communication with tip 22. Coupling 64 detachably connects aspiration line 24 to cap 62. Clip 28 fits into groove 80 of housing 14 for securing aspiration line 24 thereto by connecting to a stepped tube 116. A larger diameter tube 115 also connects to stepped tube 116.

Figure 16:
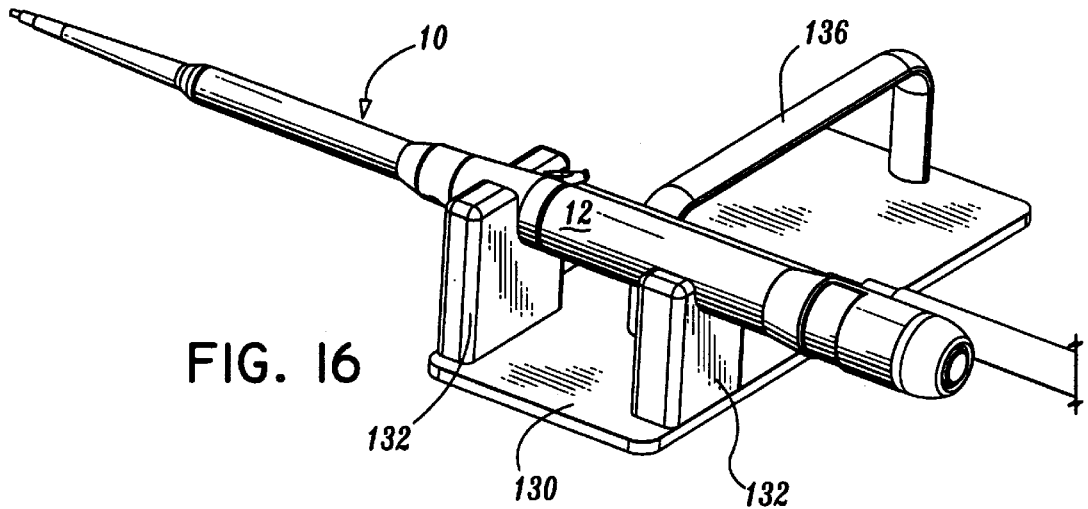
FIGS. 16 and 17 are perspective views of the surgical apparatus of FIG. 1, mounted in a tip torquing system.
Figure 17:
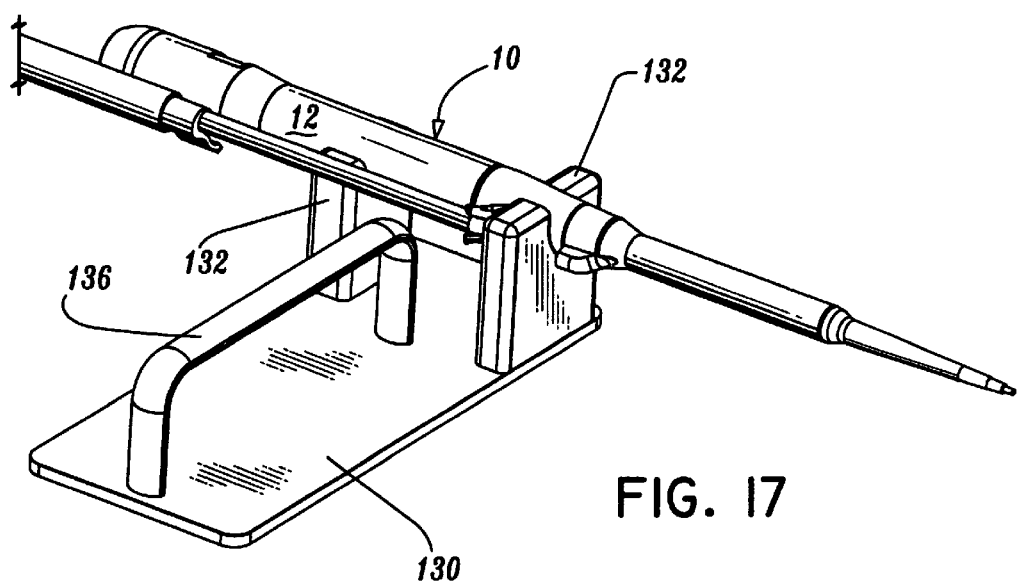

Referring to FIGS. 16 and 17, apparatus 10 is mounted in a fixture 130 for supporting apparatus 10. Fixture 130 includes bracket 132 for supporting handpiece 12 at or near node on connecting body 42. A handle 136 is provided for stabilizing supporting fixture 130 and apparatus 10. Supporting fixtures facilitates the attachment and/or removal of tools 44.

It will be understood that various modifications may be made to the embodiments disclosed herein. For example, compensation for tissue fragmentation may be provided to maintain the standing wave in apparatus 10. Further, the compensation may be provided by a compensation circuit which supplies additional current when tip 22 is in contact with tissue to maintain the standing wave. Also, guidance systems may be used to assist a surgeon during surgery, particularly neurosurgery. Therefore, the above description should not be construed as limiting, but merely as exemplifications of preferred embodiments. Those skilled in the art will envision other modifications within the scope and spirit of the claims appended hereto.

What is claimed is:

1. An improved ultrasonic surgical apparatus comprising:
    an ultrasonic handpiece, the ultrasonic handpiece defining a central longitudinal axis, the handpiece being configured and dimensioned to be less than approximately 6 inches in length and less than approximately 0.7 inches in diameter;
    a transducer housing disposed in the handpiece;
    a transducer mounted within the transducer housing and being coupled to a connecting body, the connecting body coupled with a tool having a vibratable tip for transmitting ultrasonic waves to the tip from the transducer, the connecting body being constructed of titanium or its alloys;
    a cooling system in fluid communication with the transducer housing for supplying cooling fluid to the transducer housing to substantially cool the transducer;
    an aspirating system connected to the handpiece for aspirating fluid and tissue fragmented at the surgical site; and
    an irrigation system connected to the handpiece for supplying irrigation fluid adjacent the surgical site for suspending fragmented tissue.

2. The ultrasonic surgical apparatus as recited in claim 1, wherein the transducer includes a stack of magnetostrictive plates longitudinally disposed within the handpiece and responsive to an input frequency for vibrating the tip.

3. The ultrasonic surgical apparatus as recited in claim 2, wherein the plates are flat.

4. The ultrasonic surgical apparatus as recited in claim 2, wherein the plates are gusseted.

5. The ultrasonic surgical apparatus as recited in claim 2, wherein the plates are fabricated of a material selected from the group consisting of nickel and alloys thereof.

6. The ultrasonic surgical apparatus as recited in claim 1, wherein the irrigation system further includes a fluid supply for introducing cooling fluid to a fragmenting tool.

7. The ultrasonic surgical apparatus as recited in claim 1, further including a fluid supply for introducing cooling fluid to the transducer.

8. The ultrasonic surgical apparatus as recited in claim 1, wherein the aspiration system includes a detachable aspiration line wherein the aspiration line is removable from the handpiece.

9. The ultrasonic surgical apparatus as recited in claim 1, wherein the ultrasonic handpiece further comprises an ultrasonic fragmenting tool mounted within the handpiece, the tool having a vibratable tip adapted for ultrasonically fragmenting tissue at a surgical site of a patient.

10. The ultrasonic surgical apparatus as recited in claim 9, wherein the tip has a cavity formed therein in fluid communication with at least one inlet port positionable at a location adjacent to the surgical site wherein the aspiration system aspirates fluid and tissue fragmented by the tip from the surgical site through the inlet port and cavity.

11. The ultrasonic surgical apparatus as recited in claim 1, wherein the handpiece is between about 4.5 and about 6 inches in length.

12. The ultrasonic surgical apparatus as recited in claim 1, wherein the handpiece is generally cylindrical and is between about 0.5 and about 0.7 inches in diameter.

13. The ultrasonic surgical apparatus as recited in claim 1, wherein the transducer produces standing waves having a wavelength, $\lambda$, and the transducer has a length of about $\lambda/2$, the tip has a length of about $\lambda/4$ and the connecting body has a length of about $\lambda/4$.

14. The ultrasonic surgical apparatus as recited in claim 13, wherein the handpiece is generally cylindrical and is between about 0.5 and about 0.7 inches in diameter.

15. The improved ultrasonic apparatus of claim 1, wherein the cooling system is in fluid communication with at least a portion of the connector body.

16. An improved ultrasonic surgical apparatus having increased tissue selectivity comprising:
    an ultrasonic handpiece;
    an ultrasonic fragmenting tool mounted within the handpiece, the tool having a vibratable tip adapted for ultrasonically fragmenting tissue at a surgical site of a patient and defining a longitudinal opening for removing fragmented tissue;
    a transducer mounted within the handpiece and coupled to a connecting body, the connecting body coupled with the tool for transmitting ultrasonic waves at a frequency of at least 35,000 Hz to the tip from the transducer, the connecting body having a length approximately $\lambda/4$ and defining a port in a sidewall thereof;
    an aspirating system connected to the handpiece for aspirating fluid and tissue fragmented by the tip at the surgical site, the aspirating system including an aspirating tube positioned in the port of the connecting body and in fluid communication with the longitudinal opening of the ultrasonic tool; and
    an irrigation system connected to said handpiece for supplying irrigation fluid adjacent the surgical site for suspending tissue fragmented by the tip.

17. The ultrasonic surgical apparatus as recited in claim 16, wherein the transducer includes a stack of magnetostrictive plates longitudinally disposed within the handpiece and responsive to an input frequency for vibrating the tip.

18. The ultrasonic surgical apparatus as recited in claim 17, wherein the plates are fabricated of a material selected from the group consisting of nickel and alloys thereof.

19. The ultrasonic surgical apparatus as recited in claim 17, wherein the plates are flat.

20. The ultrasonic surgical apparatus as recited in claim 16, wherein the handpiece system further includes a fluid supply for introducing cooling fluid to the transducer.

21. The ultrasonic surgical apparatus as recited in claim 16, wherein the aspiration system includes a detachable aspiration line wherein the aspiration line is removable from the handpiece.

22. The ultrasonic surgical apparatus as recited in claim 16, wherein the tip has a cavity formed therein in fluid communication with at least one inlet port positionable at a location adjacent to the surgical site wherein the aspiration system aspirates fluid and tissue fragmented by the tip from the surgical site through the inlet port and cavity.

23. The ultrasonic surgical apparatus as recited in claim 16, wherein the handpiece is between about 4.5 and about 6 inches in length.

24. The ultrasonic surgical apparatus as recited in claim 16, wherein the plates are gusseted.

25. The ultrasonic surgical apparatus as recited in claim 16, wherein the transducer produces standing waves having a wavelength, $\lambda$, and the transducer has a length of about $\lambda/2$, the tip has a length of about $\lambda/4$.

26. The ultrasonic surgical apparatus as recited in claim 16, wherein the irrigation system further includes a fluid supply for introducing cooling fluid to the fragmenting tool.

\* \* \* \* \*